United States Patent

Cossellu

[11] Patent Number: 5,257,934
[45] Date of Patent: Nov. 2, 1993

[54] ENDODONTIC INSTRUMENT FOR PREPARING THE ROOT CANAL

[76] Inventor: Giovanni Cossellu, via Padova 113, 20100 Milano, Italy

[21] Appl. No.: 857,319

[22] Filed: Mar. 25, 1992

[51] Int. Cl.⁵ ............................................. A61C 5/02
[52] U.S. Cl. .................................................. 433/102
[58] Field of Search ............................. 433/102, 224

[56] References Cited

U.S. PATENT DOCUMENTS

| | | | |
|---|---|---|---|
| 4,231,738 | 11/1980 | Riitano et al. | 433/102 |
| 4,332,561 | 6/1982 | McSpadden | 433/102 |
| 4,850,867 | 7/1989 | Senia et al. | 433/102 |
| 5,104,316 | 4/1992 | McSpadden | 433/102 |

FOREIGN PATENT DOCUMENTS

| | | | |
|---|---|---|---|
| 0257961 | 3/1988 | European Pat. Off. | 433/102 |
| 0648688 | 7/1937 | Fed. Rep. of Germany | 433/102 |
| 2524105 | 1/1976 | Fed. Rep. of Germany | 433/102 |

Primary Examiner—Gene Mancene
Assistant Examiner—Cindy A. Cherichetti
Attorney, Agent, or Firm—Wolf, Greenfield & Sacks

[57] ABSTRACT

An endodontic instrument for preparing the root canal which is suitable for being mounted on an endodontic contra-angle and with a conventional handle for manual use. The instrument is constituted by a series of broaches in which the working part is short with respect to the overall length. The instrument, by pivoting with its end portion in the apical part of the canal, which is prepared beforehand by the files, always works at the apex and prepares, in each instance, a small part of the canal, advancing progressively from the coronal inlet to the apex.

10 Claims, 2 Drawing Sheets

ENDODONTIC INSTRUMENT FOR PREPARING THE ROOT CANAL

BACKGROUND OF THE INVENTION

The present invention relates to an endodontic instrument for preparing the root canal, provided both with a coupling for mounting on an endodontic contra-angle and with a conventional handle for manual use.

The morphological aims of a good preparation of the root canal can be summarized in the following items.

1. The canal must have a truncated-cone shape with a coronal larger planar face and an apical smaller planar face.
2. During preparation it is necessary to respect the original configuration of the canal.
3. A corollary of the preceding item is that the apical foramen must maintain the same spatial relationship with respect to both the root itself and to the paradental bone.
4. The apical foramen must be kept as small as possible.

One of the instruments used to prepare the canal is the so-called "reamer", a broaching instrument which is normally constituted by a bar which has a twisted triangular cross-section whose diameter increases constantly in the apical-coronal direction of the canal.

It is evident that the achievement of these aims with conventional instruments requires the operator to provide not only considerable manual precision and skill but also a great expenditure of time, with consequent costs for the patient.

The direct consequence of all this is that many operators prefer canal preparation methods which are simpler and more rapid, even if they are burdened by a higher percentage of failures; furthermore, rational and correct endodontics cannot be part of the practice of a dentist who performs so-called "social" dentistry, regardless of the good will and skill of the operator.

In order to provide the patients with a high-level endodontic service without however increasing the costs of these therapies, it would be necessary to use instruments mounted on the contra-angle, in order to save on canal preparation times.

However, it is known that with the currently available instruments it is not possible to achieve the above aims except to a minimal extent.

For example, one of the most severe problems of instruments mounted on a contra-angle is that in curved canals they cause the apical foramen to shift and become elliptical, and that they furthermore deform the apical portion of the canal, generating a truncated-cone shape with an apical larger planar face. The truncated-cone shape of the canal prevents the optimum condensation of the gutta-percha in that point, and a correct apical seal is consequently not ensured.

SUMMARY OF THE INVENTION

The aim of the present invention is to provide an endodontic instrument which is able to overcome the above described problems and can be advantageously mounted on a contra-angle.

Within the scope of this aim, an object of the invention is to provide an instrument which allows to achieve all the described morphological aims, performing a rigorous preparation of the root canal with a great time saving.

This aim, these objects and others which will become apparent hereinafter are achieved by an endodontic instrument for preparing the root canal, characterized in that it comprises a series of broaches, each of said broaches comprising a first coronal portion, a second active broaching portion and a third apical portion, said broaching portion being arranged at a progressively greater distance from the coronal inlet for each of said broaches which constitute said series, the diameter of said broaching portion reducing correspondingly, said broaches being suitable for being used one after the other to prepare said canal, advancing progressively from the coronal inlet up to the apex.

BRIEF DESCRIPTION OF THE DRAWINGS

Further characteristics and advantages will become apparent from the description of a preferred but not exclusive embodiment of the invention, illustrated only by way of non-limitative example in the accompanying drawings, wherein.

DESCRIPTION OF THE PREFERRED EMBODIMENTS

Figure 1:
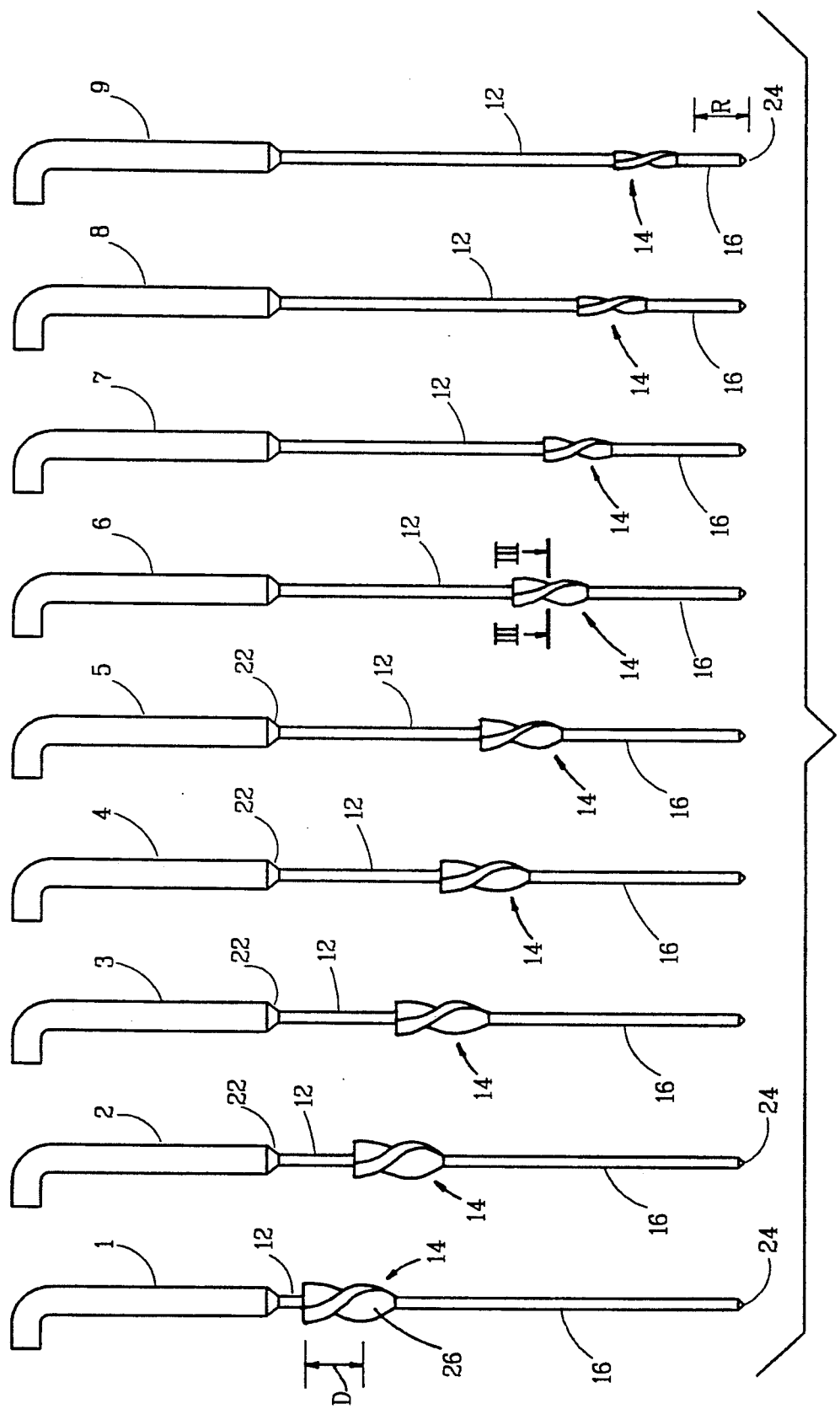
FIG. 1 is an enlarged lateral elevation view of a series of broaches which constitute the instrument according to the invention.
Figure 3:
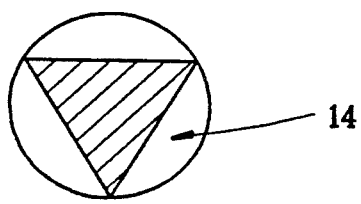
FIG. 3 is an enlarged horizontal sectional view, taken along the plane III—III of FIG. 1, of a broach of the instrument.
Figure 2:
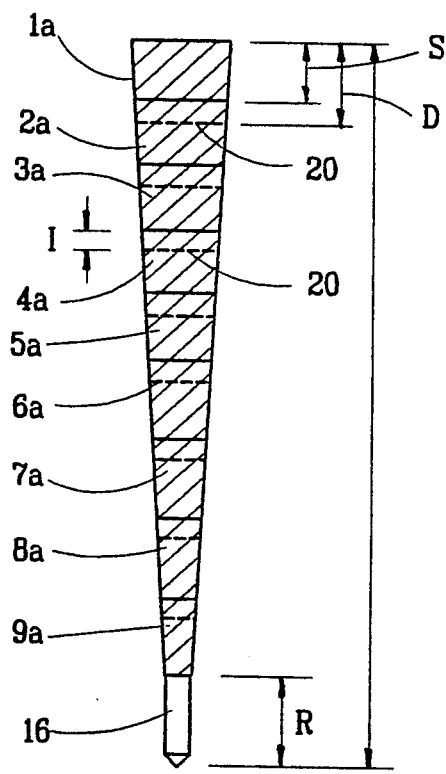
FIG. 2 is a schematic sectional side view of the relationship between the broaching portions of the various elements.

With reference to the above figures, the instrument according to the invention, generally designated by the reference numeral 10, comprises a series of broaches designated by the reference numerals 1 to 9.

Each broach comprises a first coronal portion 12, a second broaching portion 14 and a third apical portion 16. The coronal portion is connected to a tang in order to allow the connection of the broach to a contra-angle in a per se known manner.

The broaching portion has an axial extension D which is substantially small with respect to the overall length of the element, as clearly shown in FIG. 1, and its distance from the coronal inlet 22 varies and increases starting from the first element 1 up to the last element 9 of the series.

The distance S between two homologous points of the broaching portions 14 of two successive broaches is slightly smaller than the extension D of said portions 14, so that there is a certain interference I between two successive portions worked by the respective broaching portions.

The broaching portion 14 furthermore has a portion 26 for blending with the apical portion 16.

In the last element 9 of the series, the broaching portion 14 is at a minimum distance R from the apical end 24, so as to define a terminal part 16 which is termed "file reserved region" since it corresponds to a region of the canal which is prepared exclusively by files.

As shown hereinafter, as regards the use of the instrument, three basic series of the instrument are advantageously provided, according to the presumed length of the apices after they have been probed and prepared with the files in a per se known manner.

By way of example, there is preferably a first series for apices having a diameter of 0.3 mm, a second series for 0.4-mm apices and a third series for 0.5-mm apices.

Each series can furthermore advantageously comprise five sub-series, according to the diameter to be given to the canal from its coronal inlet. Said series and subseries are based on the most common presumable clinical conditions, but they may naturally be executed in numbers and types which differ from what is shown.

The instrument according to the invention is used by inserting the first broach 1 of the series in the canal, prepared beforehand by means of files, in a per se known manner, so that the apical end 24 is inserted in the apical part of the canal and acts as pivot during the rotation of the broach; the broaches 2-9 are then used in succession, preparing in each instance a small part of the canal, advancing progressively from the coronal inlet up to the apex.

An advantage of the instrument according to the invention is due to the fact that the increase in the diameter of the broaching portion is variable: in fact the operator, after preparing the apex of the canal and determining the diameter of the apical foramen, which is given by the diameter of the last instrument at the apex, determines the diameter which the coronal inlet of the canal must and can have.

It will thus be necessary to choose a series in which the tip of the inactive part, i.e. of the portion 16, has a diameter which corresponds to the diameter of the tip of the last file at the apex.

The first broach of the selected series will have, in its broaching portion, a diameter which corresponds to the diameter which, according to the operator, must be the diameter of the coronal inlet, and prepares a first part of the canal for an extent which corresponds to the extension D of the broaching portion.

By way of example, the extension D of the broaching portion is preferably 2 mm, whereas the distance S between two homologous points of the broaching portions of two successive broaches is preferably 1.5 mm.

The sum of the broaching portions of all the elements 1-9 is thus 13.5 mm, to which one must add the 1.5-mm file reserved region; overall, therefore, the preferred total length of the active portion of the instrument is 15 mm, whereas the overall length of the instrument, from the tang to the tip, can be, as for conventional instruments, 21 mm, 25 mm, 29 mm and 31 mm, depending on whether anterior or posterior teeth are involved and according to their length.

In practice it has been observed that the invention achieves the intended aim and objects by providing an instrument which can be mounted mainly on a contra-angle, allowing at the same time a rigorous preparation of the root canal, regardless of the individual skill of the operator.

The instrument according to the invention is susceptible to numerous modifications and variations, all of which are within the scope of the inventive concept; all the details may furthermore be replaced with technically equivalent elements.

The materials employed, as well as the dimensions, may naturally be any according to the requirements and the state of the art.

I claim:

1. A series of endodontic instruments for preparing a root canal, each member of said series including a broach portion, each of said broach portions comprising a first coronal portion having a coronal inlet, a second active broaching portion of a certain length and a third apical portion, said active broaching portion arranged at a progressively greater distance from the coronal inlet for each member of said series of instruments, the diameter of said active broaching portion reducing correspondingly, each said member suitable for use in sucession to prepare said root canal, said active broaching portion advancing progressively from the coronal inlet up to said apical portion, the length of the active broaching portion remaining substantially the same among members of said series of instruments.

2. The instruments according to claim 1, characterized in that said broaching portion has an axial extension which is substantially smaller than the sum of the axial extensions of said apical and coronal portions.

3. The instruments according to claim 1, characterized in that the free end of said apical portion is suitable for pivoting in the apical part of said canal.

4. The instruments according to claim 1, characterized in that the increase in the diameter of said broaching portion in the apical-coronal direction is variable.

5. The instruments according to claim 1, wherein the distance between identical points on the active cutting portions of any two successive members of the series defines an area of overlap between active cutting portions of any two successive members of the series.

6. The instruments according to claim 5, wherein said distance is constant at about 1.5 mm.

7. The instruments according to claims 1 or 6, comprising nine individual members, the sum of the active cutting portions of said nine individual members being 13.5 mm.

8. A method of preparing a root canal using a series of endodontic instruments, comprising the steps of:
   a. inserting into said root canal a member of said series, said member having a coronal inlet, and a cutting portion of a given length and diameter;
   b. cutting into said root canal using said member;
   c. removing said member from said root canal after cutting is completed;
   d. repeating steps a-c using successive members of said series, each said successive member having a progressively smaller diameter cutting portion.

9. The method of claim 8, wherein each successive cutting is a substantially identical distance downwards into said root canal, each said successive member having a substantially identical cutting portion length.

10. The method of claim 8, wherein each successive cutting is located at a progressively greater distance into said root canal, each said successive member having a cutting portion located a progressively greater distance from the coronal inlet than a previous member.

* * * * *